United States Patent
Abe et al.

(10) Patent No.: US 7,239,907 B2
(45) Date of Patent: Jul. 3, 2007

(54) DIAGNOSTIC APPARATUS, ULTRASONIC DIAGNOSTIC APPARATUS, AND OPERATION CONTROLLING METHOD THEREOF

(75) Inventors: Yoshihito Abe, Kuroiso (JP); Kenji Hamada, Otawara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/410,264

(22) Filed: Apr. 10, 2003

(65) Prior Publication Data

US 2003/0208118 A1    Nov. 6, 2003

Related U.S. Application Data

(63) Continuation of application No. PCT/JP01/08891, filed on Oct. 10, 2001.

(30) Foreign Application Priority Data

Oct. 10, 2000    (JP) .............................. 2000-308964

(51) Int. Cl.
*A61B 5/05* (2006.01)
(52) U.S. Cl. ...................... 600/407; 600/443
(58) Field of Classification Search ........ 600/407–471, 600/300–302; 73/625; 367/138; 345/2.3; 606/22
See application file for complete search history.

(56) References Cited

U.S. PATENT DOCUMENTS

| | | | | |
|---|---|---|---|---|
| 3,932,759 | A | | 1/1976 | Brundin |
| 5,315,999 | A | | 5/1994 | Kinicki et al. |
| 5,325,858 | A | * | 7/1994 | Moriizumi .................. 600/443 |
| 5,379,771 | A | | 1/1995 | Kawasaki et al. |
| 5,544,654 | A | * | 8/1996 | Murphy et al. ............. 600/443 |
| 5,553,620 | A | * | 9/1996 | Snider et al. ............... 600/440 |
| 5,603,323 | A | * | 2/1997 | Pflugrath et al. ........... 600/437 |
| 5,629,714 | A | * | 5/1997 | Nishitani et al. ............ 345/2.3 |
| 5,797,846 | A | * | 8/1998 | Seyed-Bolorforosh et al. .......................... 600/447 |
| 5,805,118 | A | * | 9/1998 | Mishra et al. ............... 345/1.1 |
| 5,868,676 | A | * | 2/1999 | McCabe et al. ............. 600/454 |
| 5,919,138 | A | * | 7/1999 | Ustuner ...................... 600/443 |
| 6,001,061 | A | * | 12/1999 | Ogishima et al. ........... 600/440 |
| 6,306,089 | B1 | * | 10/2001 | Coleman et al. ............ 600/437 |
| 6,322,505 | B1 | * | 11/2001 | Hossack et al. ............. 600/437 |
| 6,363,033 | B1 | * | 3/2002 | Cole et al. .................. 367/138 |
| 6,411,836 | B1 | * | 6/2002 | Patel et al. ................. 600/407 |
| 6,413,218 | B1 | * | 7/2002 | Allison et al. .............. 600/443 |
| 6,430,428 | B1 | * | 8/2002 | Lindstedt ................... 600/410 |
| 6,454,712 | B1 | * | 9/2002 | Oonuki ....................... 600/437 |

(Continued)

FOREIGN PATENT DOCUMENTS

GB    1 448 075    5/1974

(Continued)

*Primary Examiner*—Francis J. Jaworski
(74) *Attorney, Agent, or Firm*—Oblon, Spivak, McClelland, Maier & Neustadt, P.C.

(57) ABSTRACT

By using the input unit, a condition previously regarded necessary, for example, some parameter values of a plurality of frequencies are registered as a group. The registered parameter values are stored in a memory within the apparatus setting condition controlling unit. An operator selects a desired group at a diagnosis time, and selects a parameter value to be used for diagnosis, from a plurality of parameter values forming the group. The apparatus operates based on the operational condition defined by the parameter value, to make a diagnosis.

14 Claims, 11 Drawing Sheets

U.S. PATENT DOCUMENTS

| | | | |
|---|---|---|---|
| 6,458,081 B1 * | 10/2002 | Matsui et al. | 600/437 |
| 6,527,765 B2 * | 3/2003 | Kelman et al. | 606/22 |
| 6,603,494 B1 * | 8/2003 | Banks et al. | 345/807 |
| 6,673,015 B1 * | 1/2004 | Glover et al. | 600/437 |

FOREIGN PATENT DOCUMENTS

| | | |
|---|---|---|
| JP | 2-126226 | 10/1990 |
| JP | 4-90749 | 3/1992 |
| JP | 4-307039 | 10/1992 |
| JP | 5-253220 | 10/1993 |
| JP | 6-9606 | 2/1994 |
| JP | 9-201359 | 8/1997 |
| JP | 11-206767 | 8/1999 |

* cited by examiner

FIG. 11

SELECT THE GROUP NUMBER TO USE.

| 1 | FREQUENCY | 1, 3, 5 | 5 | | |
|---|---|---|---|---|---|
| 2 | FREQUENCY | 2, 8, 9 | 6 | | |
| 3 | | | 7 | | |
| 4 | | | 8 | | |

RETURN    NEXT    TO USUAL MODE

FIG. 12

GROUP 1 FREQUENCY 1    2    3

START SCAN

RETURN    STOP SCAN    TO USUAL MODE

DIAGNOSTIC APPARATUS, ULTRASONIC DIAGNOSTIC APPARATUS, AND OPERATION CONTROLLING METHOD THEREOF

CROSS-REFERENCE TO RELATED APPLICATIONS

This is a Continuation Application of PCT Application No. PCT/JP01/08891, filed Oct. 10, 2001, which was not published under PCT Article 21(2) in English.

This application is based upon and claims the benefit of priority from the prior Japanese Patent Application No. 2000-308964, filed Oct. 10, 2000, the entire contents of which are incorporated herein by reference.

BACKGROUND OF THE INVENTION

1. Field of the Invention

The present invention relates to a diagnostic apparatus and an ultrasonic diagnostic apparatus used for diagnosis, and the controlling method thereof.

2. Description of the Related Art

As a diagnostic apparatus for examining the body of an object, there are an ultrasonic diagnostic apparatus using ultrasound, an X-ray CT scanner using X-ray, and a magnetic resonance imaging apparatus using magnetic force. In any apparatus, various setting including the setting of frequency to be used and imaging region are required, when making a diagnosis. Recently, a color angiography for displaying the blood signal in color has become prevalent in the ultrasonic apparatus, a helical scan method of scanning spirally becomes prevalent in the X-ray CT scanner, and a lot of pulse sequences for applying magnetic fields are used in the nuclear magnetic resonance imaging apparatus. Therefore, setting condition in using the respective diagnostic devices are likely to be increased.

More specifically, for example, the ultrasonic diagnostic apparatus can be used for diagnosis of every region because of having no ill effect of exposure to radiation. Owing to this characteristic, various conditions depending on the regions to be diagnosed must be set. When taking the frequency that is one of the conditions, as an example, generally, different frequencies must be set in the examination of the abdominal region and in the examination of a fetus. Further, in many cases, various frequencies may be used according to the operator's taste or the state of a patient. Moreover, different frequencies may be used according to the display method of B mode or color mode.

In order to improve a diagnostic efficiency of a patient, or to make an urgent diagnosis in an emergency case, a quick setting of conditions is required in the diagnostic apparatus. Especially, since the ultrasonic diagnostic apparatus of a compact size can make a quick diagnosis, it is very useful as the emergency diagnostic apparatus and therefore, a quick setting of conditions is strongly desired in the ultrasonic diagnostic apparatus.

In the conventional diagnostic apparatus, however, an operator must select a condition to use from all the selectable conditions at every diagnostic time. As is often the case, an operator may change the condition such as frequency from his or her experience during the diagnosis. In this case, the operator has to select a condition to use, again, from all the conditions. Therefore, it takes an enormous time to select each setting condition of an apparatus, decreasing efficiency of diagnosis.

In order to solve the above problem, the invention is to provide a diagnostic apparatus setting method and setting means capable of setting an apparatus quickly and a diagnostic apparatus using the above method and means.

BRIEF SUMMARY OF THE INVENTION

The invention implements the following means, in order to achieve the above objects.

A first aspect of the invention is an ultrasonic diagnosis apparatus comprising: an input unit for selecting at least one frequency from a plurality of frequencies of ultrasonic pulse transmitted from an ultrasonic probe; a storing unit for storing at least the one frequency selected by the input unit as a frequency group; and a driving signal generator for generating a driving signal for driving the ultrasonic probe at the predetermined frequency specified when the input unit specifies a predetermined frequency from at least the one frequency forming the frequency group being stored.

A second aspect of the invention is an ultrasonic diagnostic apparatus comprising: a storing unit for storing a plurality of frequency groups each consisting of at least one frequency of a plurality of frequencies of ultrasonic pulse transmitted from an ultrasonic probe; an input unit for specifying a predetermined frequency group from the frequency groups and specifying a predetermined frequency from at least the one frequency forming the predetermined frequency group; and a driving signal generator for generating a driving signal for driving the ultrasonic probe at the predetermined frequency specified by the input unit.

A third aspect of the invention is an ultrasonic diagnosis apparatus comprising: an input unit for selecting two and more frequencies from a plurality of frequencies of ultrasonic pulse transmitted from an ultrasonic probe and specifying order of priority; a storing unit for storing the two and more frequencies selected by the input unit, together with the priority order, as a frequency group; and a driving signal generator for generating a driving signal for driving the ultrasonic probe at the two and more frequencies forming the frequency group, according to the priority order, when the input unit specifies the frequency group being stored.

A fourth aspect of the invention is an ultrasonic diagnosis apparatus comprising: an input unit for selecting at least one parameter value as for a parameter as an operational condition of the apparatus; a storing unit for storing at least the one parameter value selected by the input unit as an operational condition group; and a controlling unit for generating a signal for controlling the apparatus at the predetermined parameter value specified when the input unit specifies a predetermined parameter value from at least the one parameter value forming the operational condition group being stored.

A fifth aspect of the invention is an ultrasonic diagnostic apparatus comprising: a storing unit for storing a plurality of operational condition groups each consisting of at least one parameter value as for a predetermined parameter as an operational condition of the apparatus, an input unit for specifying a predetermined operational condition group from the operational condition groups and specifying a predetermined parameter value from at least the one parameter value forming the predetermined operational condition group; and a controlling unit for generating a signal for controlling the apparatus at the predetermined parameter value specified by the input unit.

A sixth aspect of the invention is an ultrasonic diagnosis apparatus comprising: an input unit for specifying at least one combination set of parameter values as for an operation condition of the apparatus defined by a combination of at least two or more kinds of parameters; a storing unit for storing at least the one combination set of parameter values specified by the input unit as an operational condition group; and a controlling unit for generating a signal for controlling the apparatus according to the predetermined combination of parameter values specified, when the input unit specifies a predetermined combination of parameter values from at least the one combination set of parameter values forming the operational condition group being stored.

A seventh aspect of the invention is an unltrasonic diagnostic apparatus comprising: a storing unit for storing a plurality of operational condition groups each consisting of at least one combination set of parameter values as for an operational condition of the apparatus defined by a combination of at least two or more kinds of parameters; an input unit for specifying a predetermined operational condition group from the operational condition groups and specifying predetermined combination of parameter values from at least the one combination set of parameter values forming the predetermined operational condition group; and a controlling unit for generating a signal for controlling the apparatus in the predetermined combination of parameter values specified by the input unit.

An eighth aspect of the invention is a diagnosis apparatus comprising: an input unit for selecting at least one parameter value as for a parameter as an operational condition of the apparatus; a storing unit for storing at least the one parameter value selected by the input unit as an operational condition group; and a controlling unit for generating a signal for controlling the apparatus at the predetermined parameter value specified when the input unit specifies a predetermined parameter value from at least the one parameter value forming the stored operational condition group.

A ninth aspect of the invention is a diagnosis apparatus comprising: a storing unit for storing a plurality of operational condition groups each consisting of at least one parameter value as for a parameter as an operational condition of the apparatus; an input unit for specifying a predetermined operational condition group from the operational condition groups and specifying a predetermined parameter value from at least the one parameter value forming the predetermined operational condition group; and a controlling unit for generating a signal for controlling the apparatus at the predetermined parameter value specified by the input unit.

A tenth aspect of the invention is an operation controlling method of an ultrasonic diagnosis apparatus, comprising: a step of selecting at least one frequency from a plurality of frequencies of ultrasonic pulse transmitted from an ultrasonic probe; a step of registering at least the one frequency selected by the input unit as a frequency group; a step of specifying a predetermined frequency from at least the one frequency forming the frequency group being registered; and a step of driving the ultrasonic probe at the specified predetermined frequency.

An eleventh aspect of the invention is an operation controlling method of an ultrasonic diagnostic apparatus, comprising: a step of specifying a predetermined frequency group from a plurality of frequency groups each consisting of at least one frequency of a plurality of frequencies of ultrasonic pulse transmitted from an ultrasonic probe; a step of specifying a predetermined frequency from at least the one frequency forming the predetermined frequency group; and a step of driving the ultrasonic probe at the specified predetermined frequency.

A twelfth aspect of the invention is an operation controlling method of a diagnosis apparatus, comprising: a step of selecting at least one parameter value as for a parameter as an operational condition of the apparatus; a step of storing at least the one parameter value selected above, as an operational condition group; a step of specifying a predetermined parameter value from at least the one parameter value forming the operational condition group being stored, by the input unit; and a step of controlling the apparatus at the specified predetermined parameter value.

A thirteenth aspect of the invention is an operation controlling method of a diagnosis apparatus, comprising: a step of specifying a predetermined operational condition group from a plurality of operational condition groups each consisting of at least one parameter value as for a parameter as an operational condition of the apparatus; a step of specifying a predetermined parameter value from at least the one parameter value forming the predetermined operational condition group; and a step of controlling the apparatus at the specified predetermined parameter value.

BRIEF DESCRIPTION OF THE SEVERAL VIEWS OF THE DRAWING

FIG. 11 shows an example of the display screen at a time of selecting a group in the embodiment.

FIG. 12 shows a screen example for selecting a parameter value in the embodiment.

DETAILED DESCRIPTION OF THE INVENTION

Figure 1A:
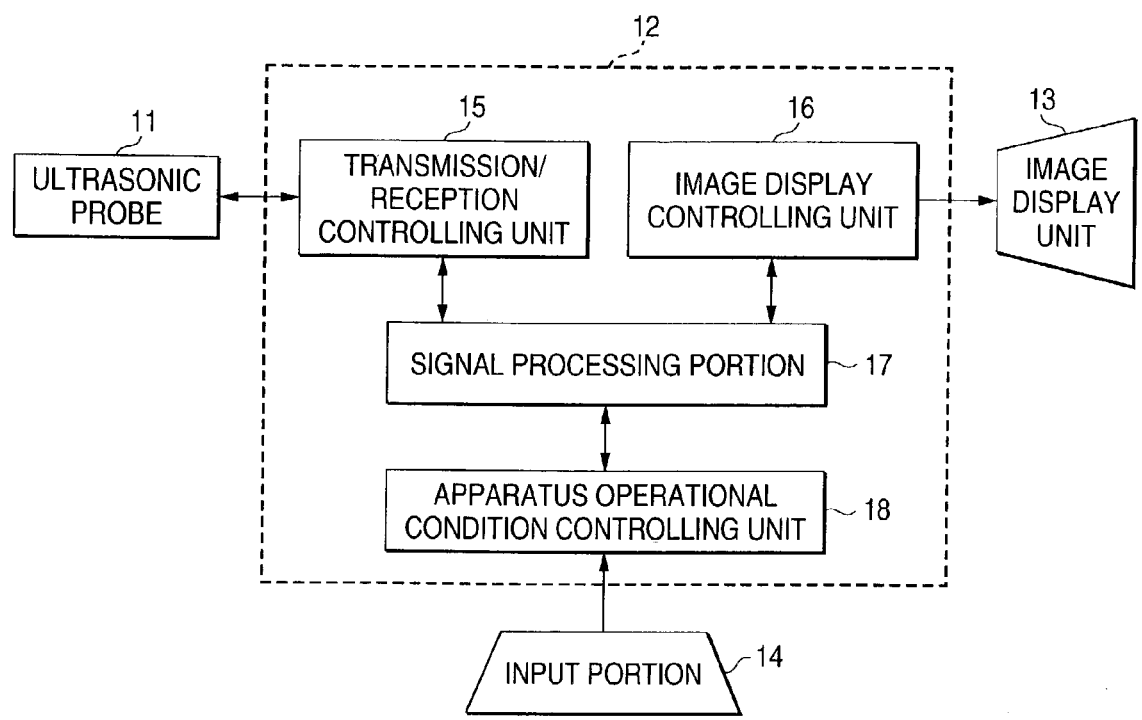
FIG. 1A is a block diagram of an ultrasonic diagnostic apparatus 12 that is one of the diagnostic apparatuses according to an embodiment.

Hereinafter, an embodiment according to the invention will be described in detail with reference to the drawings. FIG. 1A is a block diagram of an ultrasonic diagnostic apparatus 12 that is one of the diagnostic apparatuses according to the embodiment. In the following description, although the description will be made by taking the ultrasonic diagnostic apparatus 12 as an example, the technical sprit of the invention is not restricted to this ultrasonic diagnostic apparatus 12, but it can be applied to various diagnostic apparatuses such as an X-ray CT scanner, a magnetic resonance imaging apparatus, an X-ray diagnostic apparatus, and a nuclear medicine apparatus.

The ultrasonic diagnostic apparatus 12 comprises an ultrasonic probe 11, an image display unit 13, an input portion 14, a transmission/reception controlling unit 15, an image display controlling unit 16, a signal processing unit 17, and an apparatus operational condition controlling unit 18.

The ultrasonic probe 11 has a piezoelectric transducer as an acoustical/electrical reversible sensing element such as piezoelectric ceramic. A plurality of piezoelectric transducers mounted on the distal end of the probe 11, in parallel, generate ultrasound, according to a voltage pulse applied from the transmission/reception controlling unit 15.

The image display unit 13 is a monitor formed by CRT and the like, showing the tomographic image indicating the biologic tissues of a test body, according to the input video signals.

The input portion 14 is provided with an input unit (mouse and trackball, mode switch, TCS: Touch Command Screen, keyboard, and the like) for setting the region of interest (ROI) by taking various instructions and information from an operator into the apparatus 12. A predetermined instruction in the grouping processing or the group selecting processing described later is executed through the input portion 14.

The transmission/reception controlling unit 15 includes a pulse generator, a transmission delay circuit, and a pulser as a transmission system, and it is connected to the ultrasonic probe 11. The pulse generator generates rate pulses repeatedly, for example, at the rate frequency fr Hz of 5 kHz (cycle; 1/fr second). The rate pulses are distributed among the number of channels and then, sent to the transmission delay circuit. The transmission delay circuit gives a delay time interval necessary for converging the ultrasound like a beam and determining the sending directivity, to the respective rate pulses. A trigger from a trigger signal generator, not illustrated, is supplied to the transmission delay circuit, as a timing signal. The pulser applies a voltage pulse to the probe 11 in every channel at a timing of receiving the rate pulse from the transmission delay circuit. In these ways, the ultrasound beam is transmitted to the object.

The transmission/reception controlling unit 15 includes a pre-amplifier as a receiving unit, an A/D converter, a reception delay circuit, and an adder. The pre-amplifier amplifies an echo signal taken into the transmission/reception controlling unit 15 through the probe 11, in every channel. The amplified echo signal is given a delay time interval necessary for the reception delay circuit to determine the receiving directivity and the addition is executed by the adder. The above addition generates an echo signal (RF signal) with the reflection component from the direction depending on the receiving directivity of the echo signal being emphasized.

The display controlling unit 16 receives a signal graphically processed by the signal processing unit 17 and converts the signal string of the scanning line of the ultrasonic scan into the signal string of the scanning line of the general video format represented by TV. The ultrasonic image is combined with the character information of various setting parameters and a scale in the display controlling unit 16 and supplied to the image display unit 13 as a video signal.

The signal processing unit 17 includes a B mode signal processing unit and a color Doppler signal processing unit. The B mode processing unit performs the logarithmic amplification of the echo signal and the envelope detection and creates a data signal for representing signal intensity by the brightness. The color Doppler signal processing unit analyzes the frequency of the velocity information from the echo signal and supplies the analytical result to the image display controlling unit 16.

The apparatus operational condition controlling unit 18 processes a signal entered by an operator through the input portion 14 such as a keyboard and sends it to the signal processing unit 17.

Figure 1B:
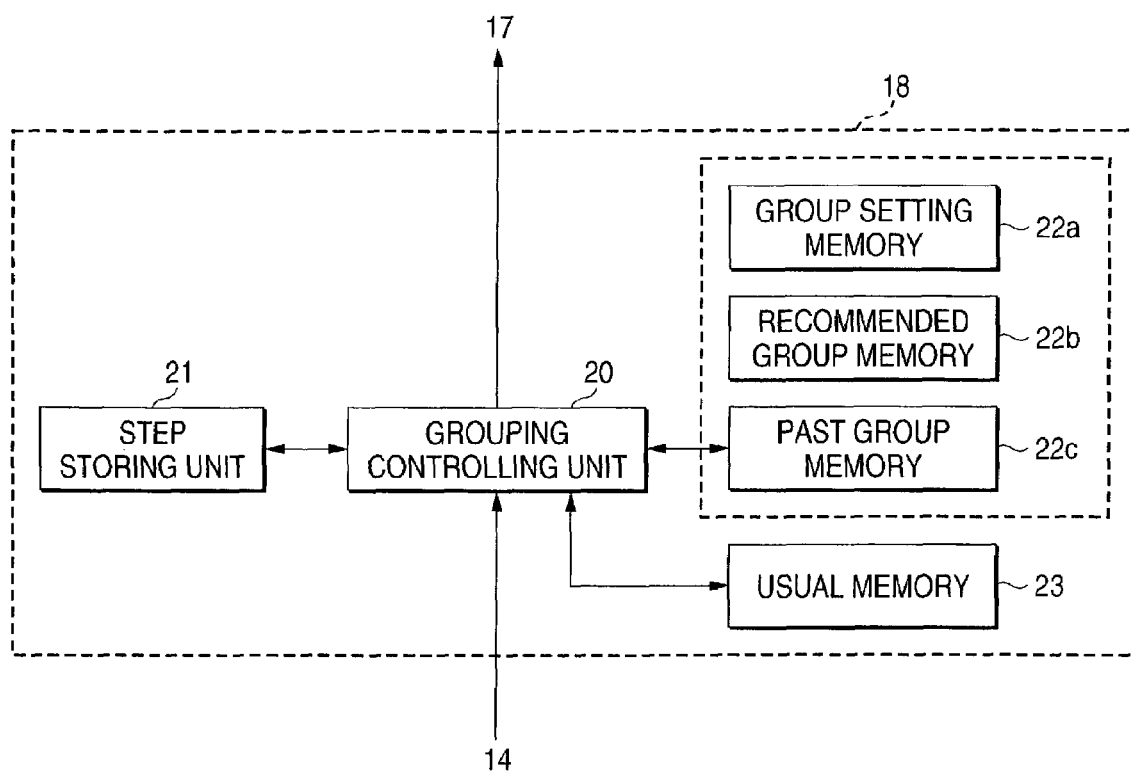
FIG. 1B is a block constitutional view of an apparatus operational condition controlling unit 18.

FIG. 1B shows a block constitutional view of the apparatus operational condition controlling unit 18. In FIG. 1B, the apparatus operational condition controlling unit 18 includes a grouping controlling unit 20, a step storing unit 21, a group memory 22, and an ordinary memory 23.

The grouping controlling unit 20 controls the group selecting and registering processing of the operational conditions described later.

The step storing unit 21 is a memory for storing the current processing state in the group selecting and registering processing of the operational conditions described later.

The group memory 22 is a memory for storing various operational conditions classified into every group. The group memory 22 includes a group registration memory 22a, a recommended group memory 22b, and a past group memory 22c, in order to control the various operation conditions in every attribute.

The group registration memory 22a is a memory for storing the newly registered group in the group selecting and registering processing described later. In reply to a predetermined operation such as end of application, the information within the group registration memory 22a is automatically transferred to the past group memory 22c.

The recommended group memory 22b is a memory for storing various operational conditions previously registered (for example, in the manufacturing step before going on sale) as a recommended group.

The past group memory 22c is a memory for storing various operational conditions having been registered as a group in the past.

The ordinary memory 23 is a memory for storing the information about the conventional mode (hereinafter, referred to as "ordinary mode") of selecting some frequency from all the usable frequencies at a diagnostic time and using it.

The group memory 22, or its components; the group registration memory 22a, the recommended group memory 22b, and the past group memory 22c, and the ordinary memory 23 may be formed in any shape such as a hard disk, FD, CD, and MD as long as it can store and provide electric data. From the viewpoint of preventing data deletion owing to malfunction, the recommended group memory 22b or the ordinary memory 23 may be formed in a read-only storing medium. When the respective memories are removable storing mediums, the information can be shared with the other ultrasonic diagnostic apparatus at ease. Further, it may be constituted in that the data within the respective memories is transferred to the external peripheral equipment, via a wired or a wireless network, not illustrated.

(Group Selecting and Registering Processing of Operational Condition)

This time, the group selecting and registering processing of the operational condition of a diagnostic apparatus, executed by this ultrasonic diagnostic apparatus 12, will be described. The operational condition of the diagnostic apparatus means the set values of the parameters for executing the diagnostic operation including the transmitted pulse frequency, the depth of viewing field, the imaging mode, and the physical index (for example, the value of MI). Hereafter, for brief description, the group selecting and registering processing of the transmitted pulse frequency will be described.

This ultrasonic diagnostic apparatus 12 can group at least one desired parameter value and more and the types of modes in every predetermined operational condition of the diagnostic apparatus. For example, as illustrated on the left side of FIG. 2, assume that the ultrasonic diagnostic apparatus 12 can use five frequencies from the frequency A to the frequency E.

There is the case where the frequency which is often used and the frequency which is rarely used are determined depending on a diagnostic object. In this case, it is more efficient to register a frequency group often used for every diagnostic object and select a proper frequency from the frequency group, for example, like the group 1 or the group 2 shown in FIG. 2, than to select a proper one from all the frequencies at every time of diagnosis.

Figure 2:
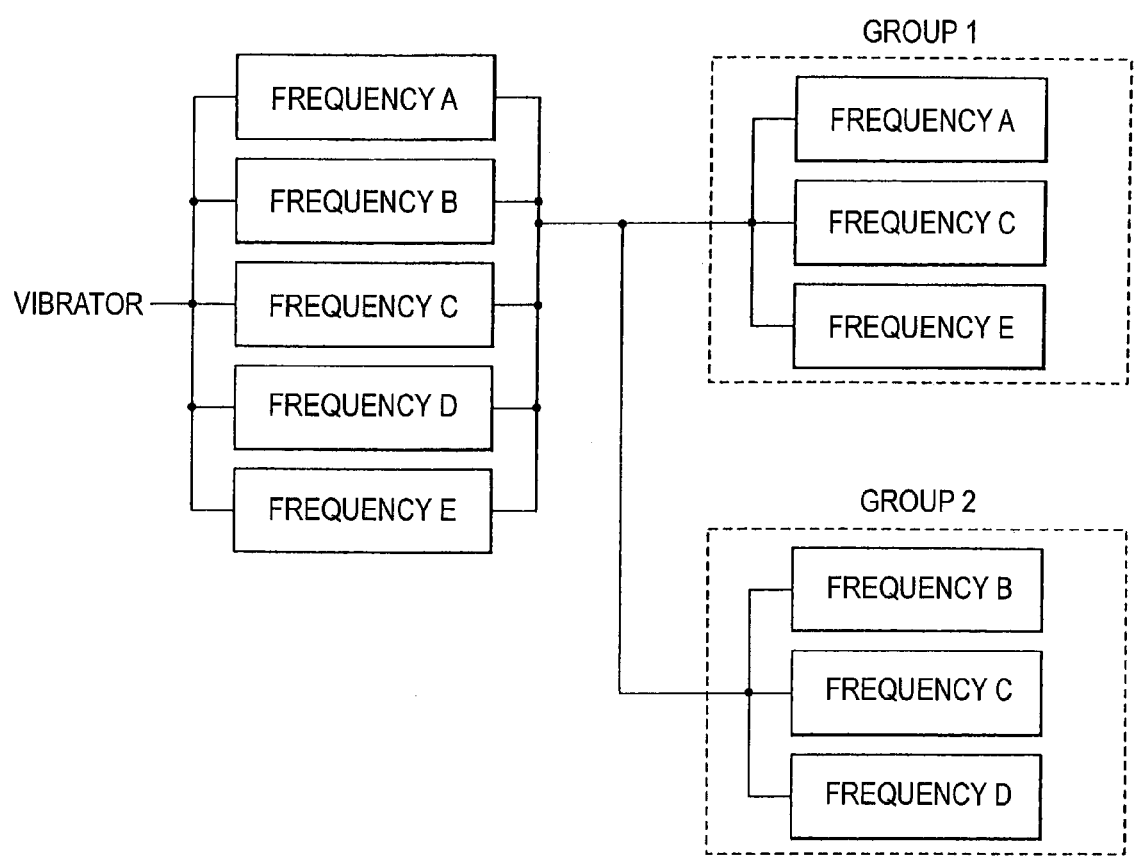
FIG. 2 is a view for use in describing grouping of the operational conditions.

Namely, in the group 1 of FIG. 2, for example, the frequencies A, C, and E used by an operator who mainly examines the abdominal region are gathered together and at a diagnostic time, the operator can select one from the frequencies A, C, and E only. The groups 1 and 2 can be changed by a switch at any time. Needless to say, the number of the groups is not restricted to two.

The group selecting and registering processing is the processing for this grouping (registration of the group) and selecting a group at a scanning time. Hereafter, the concrete contents will be described with reference to FIG. 3 to FIG. 12.

Figure 3:
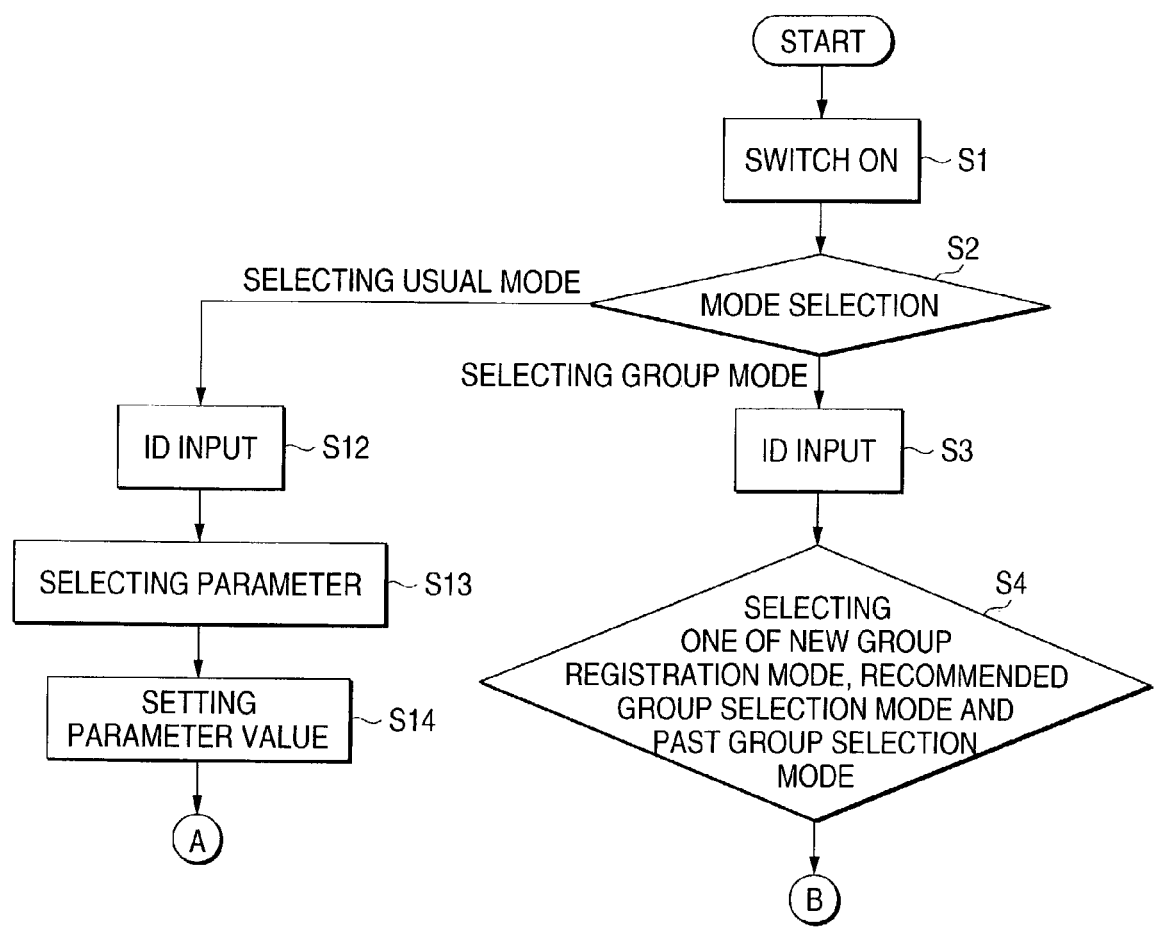
FIG. 3 is a flow chart showing the procedure of the group selecting and registering processing executed by this ultrasonic diagnostic apparatus 12.
Figure 4:
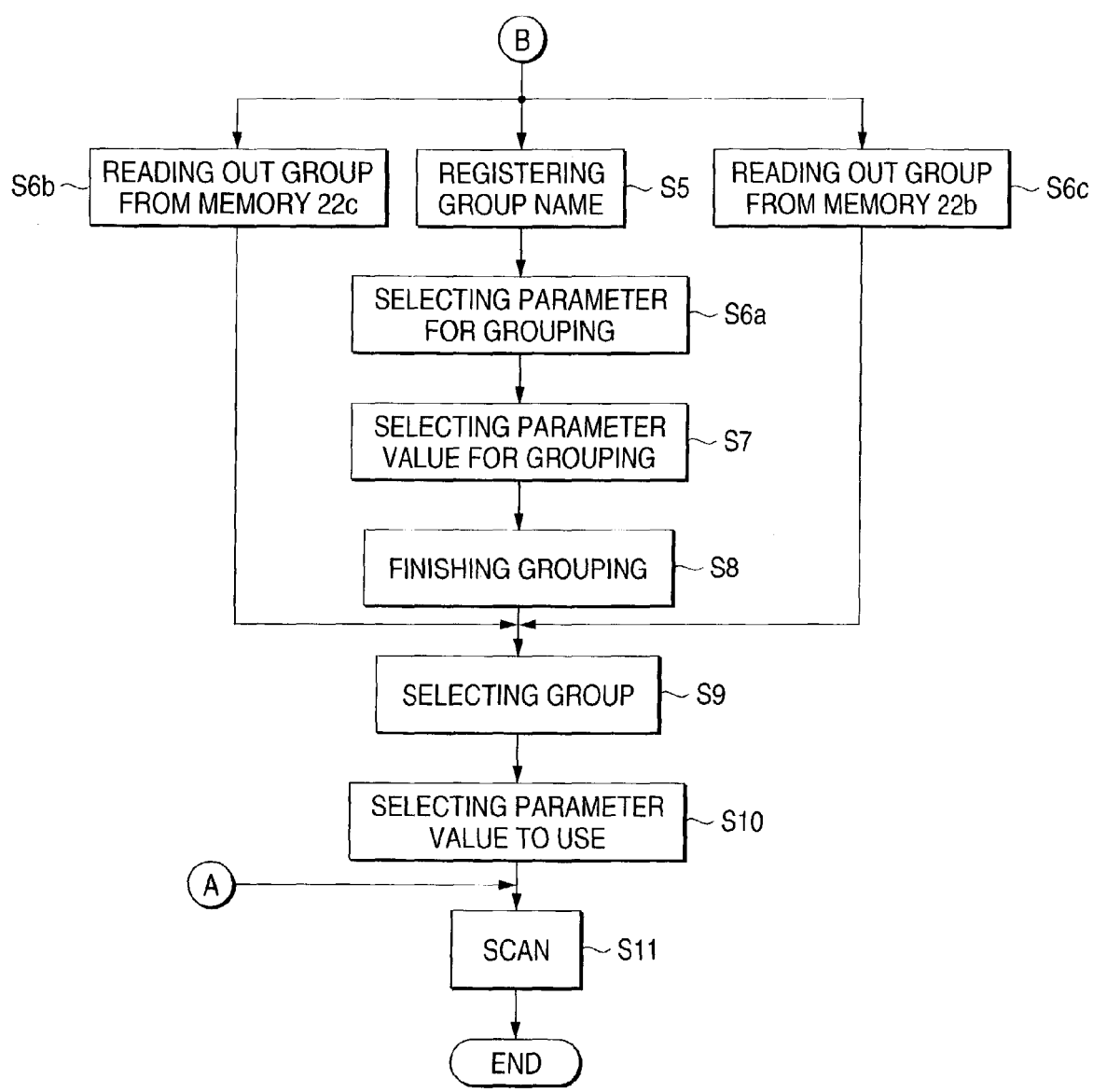
FIG. 4 is a flow chart showing the procedure of the group selecting and registering processing executed by this ultrasonic diagnostic apparatus 12.

FIG. 3 and FIG. 4 are flow charts showing the procedure of the group selecting and registering processing executed by this ultrasonic diagnostic apparatus 12.

Figure 5:
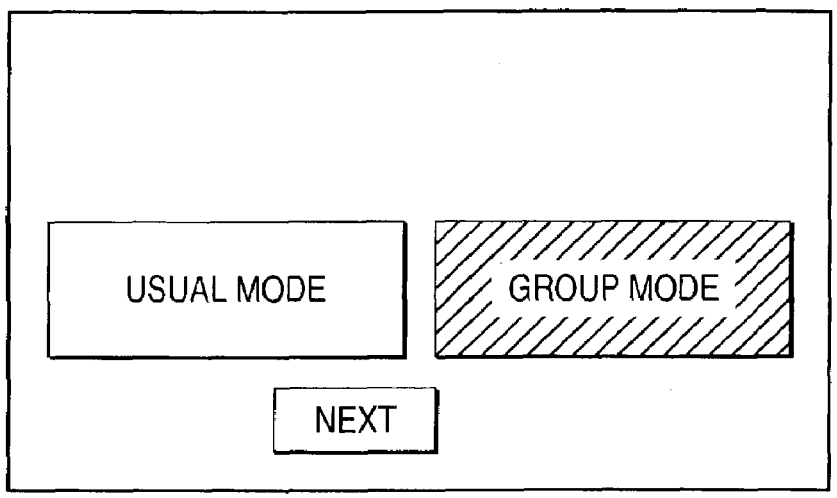
FIG. 5 is an example of the display screen at a time of selecting the ordinary mode or the group mode in the embodiment.

At first, the ultrasonic diagnostic apparatus 12 is turned on (Step S1), the ordinary mode or the grouped frequencies is selected, and one of the imaging modes to be used (hereinafter, referred to as "group mode") is selected (Step S2). One example of the image display unit 13 or the display screen of TCS at this selecting time is shown in FIG. 5.

When selecting the ordinary mode in Step S2, information such as ID is entered (Step S12). Continuously, as it is the ordinary mode, a necessary operational condition is selected from the ordinary memory 23 (Steps S13 and S14), hence to execute the ultrasound diagnosis (Step S11).

While, when selecting the group mode in Step S2, information such as ID is entered (Step S3). Continuously, the grouping controlling unit 20 displays a screen, for example, shown in FIG. 6 and one of the new group registration mode, the recommended group selection mode, and the past group selection mode is selected (Step S4).

The new group registration mode is a mode for making a new group of the operational conditions without using the operational conditions having been already grouped. In this mode, the group registration memory 22a of FIG. 2 is mainly used. The recommended group selection mode is a mode for selecting a recommended group previously stored in the recommended group memory 22b. The past group selection mode is a mode for selecting a desired group from the groups, for example, having been already registered in this ultrasonic diagnostic apparatus 12 and stored in the past group memory 22c.

Figure 6:
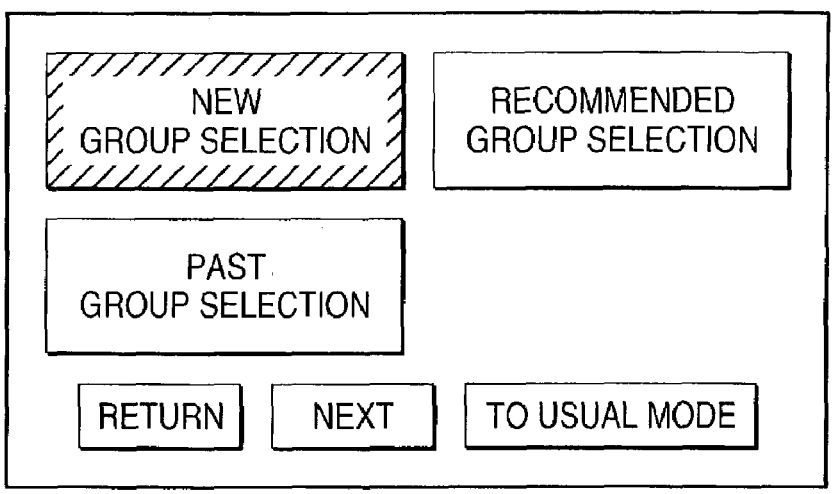
FIG. 6 is an example of the display screen at the time of selecting a new group registration mode, a recommended group selection mode, and a past group selection mode in the embodiment.

Hereinafter, the description will be made respectively in the case of selecting the new group registration mode, the case of selecting the recommended group selection mode, and the case of selecting the past group selection mode in Step S4. The display state of the button corresponding to the selected mode is changed as illustrated in FIG. 6.

Figure 7:
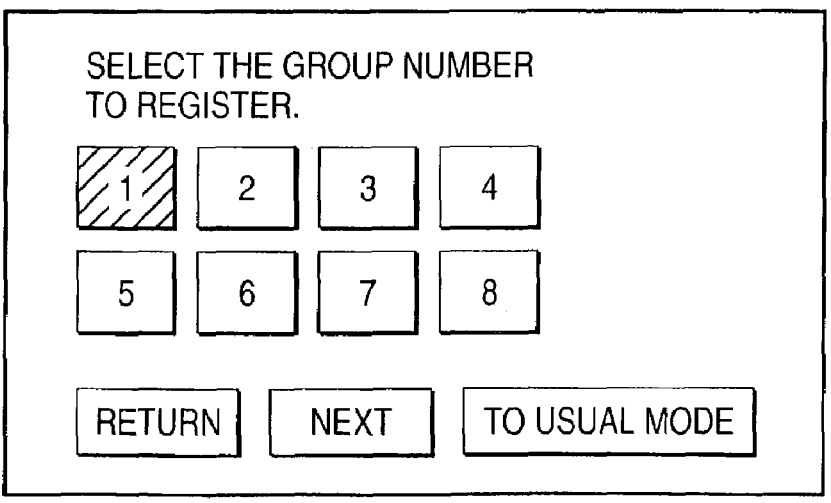
FIG. 7 shows an example of the display screen at an input time of the number for identifying a group in the embodiment.

When selecting the new group registration mode in Step S4, the number or the group name for identifying a group to be newly registered is registered (Step S5). The group name may take an individual name of an operator or the scan region. At the time, the grouping controlling unit 20 controls the display screen of the image display unit 13 as shown in FIG. 7. In FIG. 7, an example of selecting one from the number 1 to the number 8 is shown, as the number for identifying a group.

Figure 8:
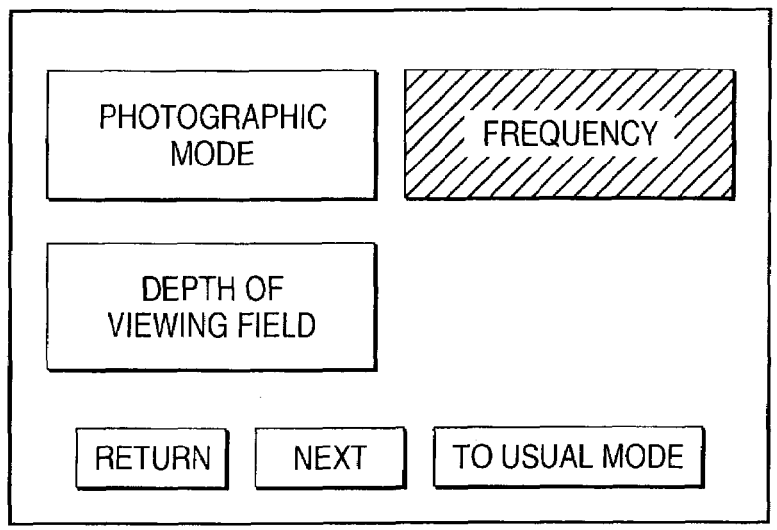
FIG. 8 shows an example of a screen for selecting three parameters including the imaging mode, frequency, and depth of viewing field in the embodiment.

A parameter for grouping is selected (Step S6a). In the embodiment, although an example of using the transmitted pulse frequency as a parameter is shown, the other parameter, for example, the imaging region may be used. FIG. 8 shows a screen example for selecting three parameters: the scan field, the frequency, and the depth of viewing field. The screen is shown on the image display unit 13 according to a control of the grouping controlling unit 20. The imaging mode means a mode for imaging and display, such as B mode, M mode, and C mode (color Doppler mode), and the depth of viewing field means the scannable depth within an object.

As for the parameter selected in Step S6a, a parameter value or contents to be registered as a group is selected (Step S7). Here, the parameter value indicates the numeric value in each parameter. For example, when the photoimaging mode is used as the parameter, the parameter value means the respective B, M, and C modes. When the frequency is used as the parameter, it means the respective frequency values. When the depth of viewing field is used as the parameter, it means the respective values of the viewing field depth. All the selectable parameter values are stored previously in the ordinary memory 23.

Figure 9:
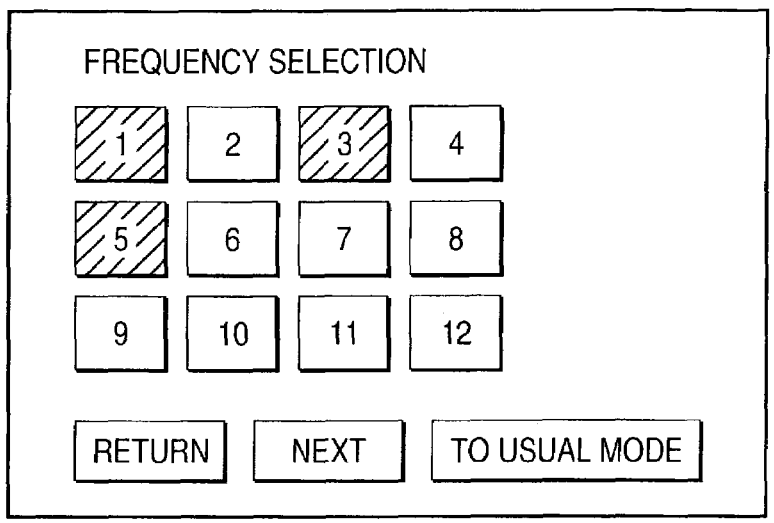
FIG. 9 shows an example of the display screen of an image display unit 13, for selecting the frequency for grouping, in the embodiment.

FIG. 9 shows an example of a display screen on the image display unit 13 for selecting the grouping frequency from 1 MHz to 12 MHz every 1 MHz. In FIG. 9, when selecting three frequencies, 1, 3, and 5 MHz, from 1 to 12 MHz, and registering the above as the first group, it is one of the above three frequencies only that an operator can select if selecting the first group at a diagnostic time. Accordingly, a trouble of selecting a frequency to use from a lot of values can be saved, thereby speeding up the diagnostic work.

Figure 10:
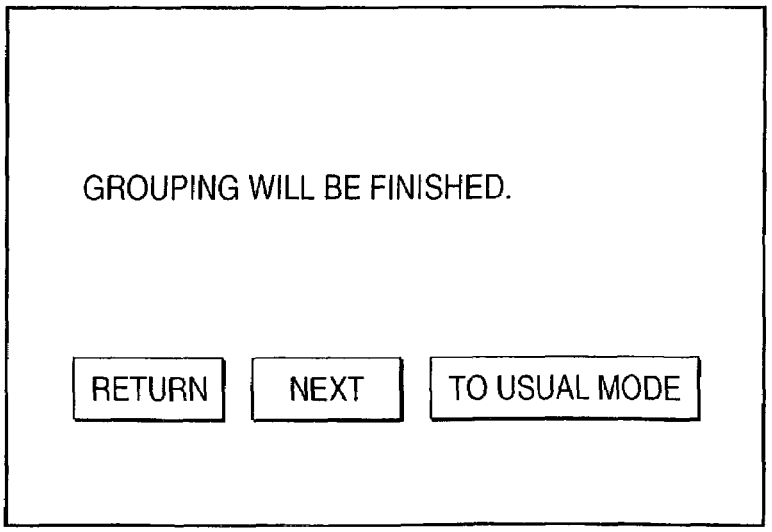
FIG. 10 shows a display example of a message to the effect that the grouping is finished, in the embodiment.

According to a predetermined operation, based on the information in the respective steps recorded in the group registration memory 22a, the information of the groups entered in Steps S5 to S7 is read out from the ordinary memory 23 and stored in the group memory 22a, hence to finish the grouping (Step S8). At this time, it is preferable that a message to the effect that the grouping will be finished, for example, as shown in FIG. 10, is displayed on the image display unit 13.

When finishing the grouping, a group to use is selected from the groups stored in the memory (Step S9). Here, it is selected, based on the group number, or the other input item, if the other identifiable item is entered, set in Step S5. FIG. 11 shows an example of a screen for selecting a group, displayed on the image display unit 13 in Step S9.

Next, a parameter value used for a diagnosis is selected (Step S10), from the group selected in Step S9. FIG. 12 shows an example of a screen for selecting a parameter value, displayed on the image display unit 13 in Step S10. As illustrated in FIG. 12, the first group consists of only the frequencies of 1, 3, and 5 MHz registered in Step 7.

After selecting a parameter value in Step S10, by pushing the button "SCAN START" shown in FIG. 12, the apparatus is set depending on the selected parameter value and a scan starts (Step S11). More specifically, the selected parameter value is sent to the transmission/reception controlling unit 15, or the image display controlling unit 16, or the other unit to be set if setting the other unit, through the signal processing unit 17 shown in FIG. 1, and the respective units are set hence to start a scan.

The ultrasonic image displayed in the left central portion of FIG. 12 indicates the scanning result. It is preferable to display the operational condition at this scan, together with the ultrasonic image, on the image display unit 13.

When finishing the scan, the finishing operation is performed in reply to a predetermined operation. At the time, the record in the group registration memory 22a is moved to the past group memory 22c.

As mentioned above, the case of selecting the new group registration mode in Step S4 has been described. The case of selecting the recommended group selection mode in Step S4 and the case of selecting the past group selecting mode will be described below.

When selecting the recommended group selection mode in Step S4, the group previously stored in the recommended group memory 22b is read out and displayed, for example, in the form shown in FIG. 11. An operator selects one proper group (Step S9), from the groups stored in the recommended group memory 22b according to the same operation, selects a parameter value of the above group (Step S10), and starts the scan (Step S11). When a group especially used for an emergency is stored in the recommended group memory 22b, it is possible to cope with the emergency case quickly.

When selecting the past group selection mode in Step 42, only the registered group having been stored previously in the past group memory 22c is read out and displayed, for example, in the form shown in FIG. 11. An operator selects one proper group (Step S9), from the groups stored in the past group memory 22c according to the same operation, selects a parameter value of the above group (Step S10), and starts the scan (Step S11). A group especially used for an emergency may be stored in the past group memory 22c.

According to the above-mentioned group selecting and registering processing of an operational condition, the following effects can be obtained.

Regardless of who is an operator or what condition a patient is in, since the choices for setting an apparatus have been the same under all the situations in the conventional art, it has taken an enormous time to select a parameter value. According to this ultrasonic diagnostic apparatus 12, however, the parameter values of the parameters are grouped together, prior to a diagnosis, and therefore, it is possible to select a necessary parameter value from the grouped parameter values at a diagnostic time. Accordingly, it is possible to set the apparatus quickly depending on the situation. As a result, the efficiency of a diagnosis can be improved. This is very useful especially in the case of an emergency.

Although the ultrasonic probe 11 and the input portion 14 are formed separately in this embodiment, the ultrasonic probe 11 may be provided with a function of the input portion 14. For example, a function of selection, like a trackball having a function belonging to the mouse, of the functions of the input portion 14, may be provided on the external lateral side of the ultrasonic probe 11. In this case, by rotating the trackball, the position of a pointer is moved on a screen, and by pushing the trackball, the corresponding item can be determined.

In this way, when the function of the input portion 14 is provided in the ultrasonic probe 11, it is not necessary for an operator to operate the ultrasonic probe 11 and the input portion 14 as each separate unit. Accordingly, the operator can set the apparatus directly through the ultrasonic probe 11, thereby speeding up a diagnosis.

By entering the identifier such as ID number assigned to each operator through the input portion 14, the individual operators can use the different groups.

FIRST MODIFIED EXAMPLE

A modified example of the embodiment will be described with reference to the drawings. The first modified example is not the form of selecting a specified one of the grouped parameter values and using it but the form of using all the grouped parameter values in a predetermined order.

Figure 13:
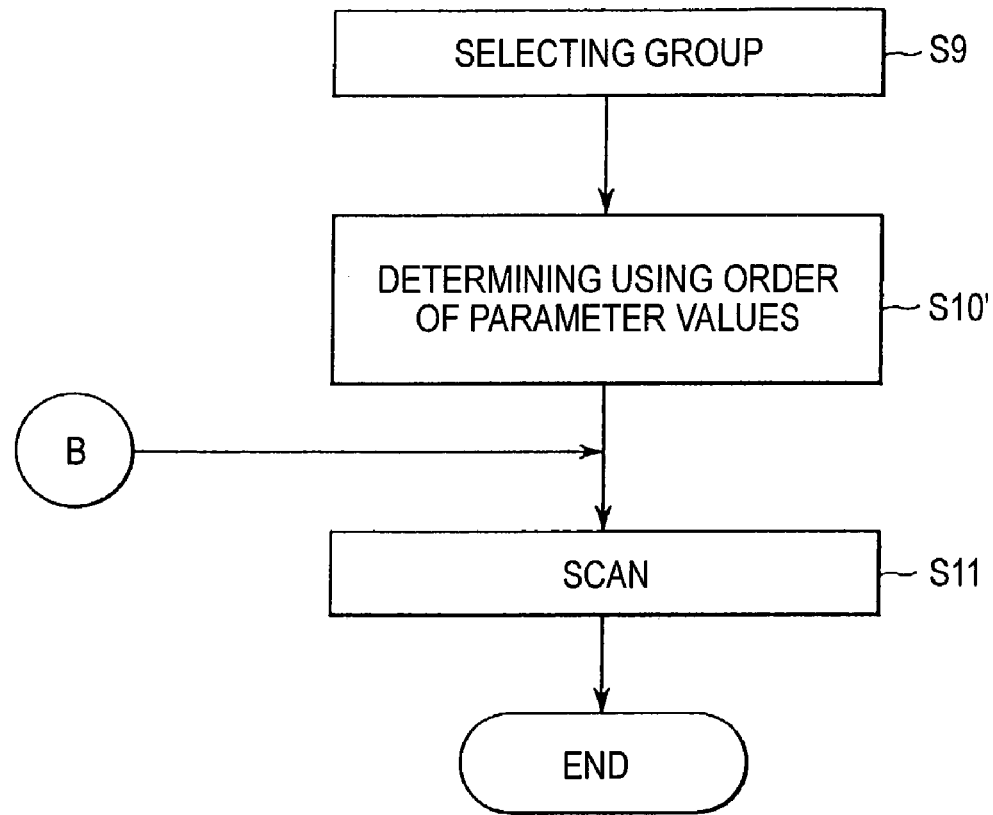
FIG. 13 is a flow chart showing the group selecting and registering processing in a first modified example.

FIG. 13 is a flow chart showing the group selecting and registering processing in the modified example. In this figure, the processing up to Step S9 is the same as the processing shown in FIG. 3 and FIG. 4.

Figure 14:
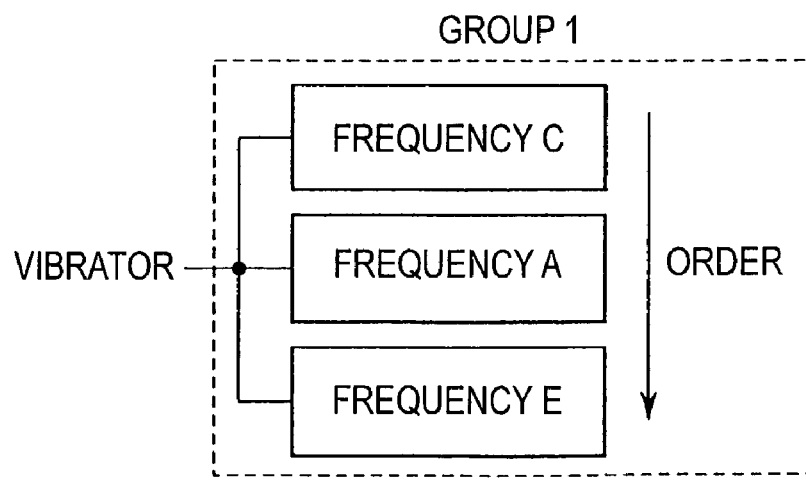
FIG. 14 is a view for use in describing the order of selecting the frequencies in the first modified example.
Figure 15:
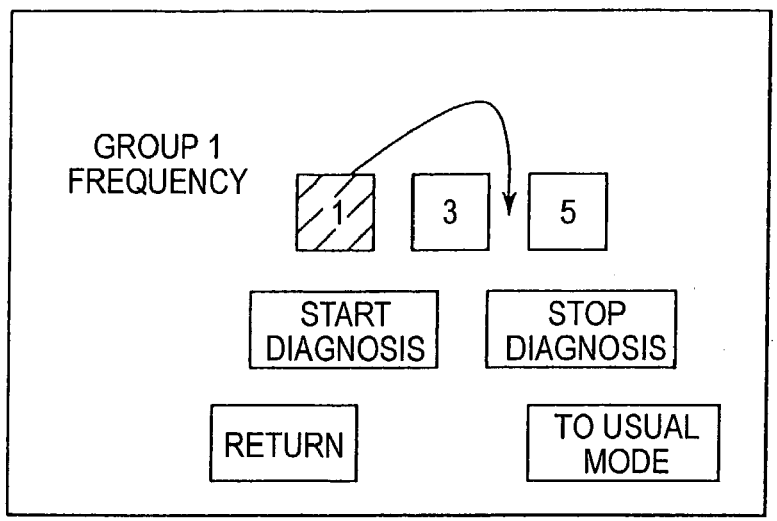
FIG. 15 is a view for use in describing a change of the order of the frequencies in the first modified example.

In FIG. 13, after selecting a group in Step S9, a selecting order of the parameter values within the group is determined (Step S10'). The selecting order may be determined freely by an operator, or it may be automatically determined, like a decreasing order. For example, as illustrated in the group 1 shown in FIG. 2, when the frequencies A, C, and E are grouped together, the order may be determined as the order of the frequencies A, C, and E, or it may be determined as the order of the frequencies C, A, and E, as illustrated in FIG. 14. The selecting order can be determined concretely in a way of, with the frame of the frequency 1 MHz selected, dragging and dropping the above frame to the portion indicated by an arrow, and as a result, the selecting order becomes the frequencies 3 MHz, 1 MHz, and 5 MHz.

A scan is executed (Step S11) this time. In the modified example, differently from the embodiment, the frequencies 1, 3, and 5 MHz are switched and used in the selecting order determined in Step 10', instead of selecting some frequency arbitrarily. Switching for use is performed by the input portion 14.

In the scan in Step 38, the case of switching the order of using the parameter values to the selecting order determined in Step 10' is shown. In addition to the selecting order determined in Step 10', an inverse order to the above selecting order can be adopted to switch the parameter value. According to this structure, in the case of selection failure or when an operator wants to scan once more with the parameter value just ahead of the current value, it is not necessary to take a round of the parameter values, according to the regular order. Accordingly, a necessary parameter value can be selected more quickly. Namely, when the frequency is determined, for example, in the order of A, C, and E, if selecting the frequency E by mistake although the frequency C has to be selected, the frequency C cannot be selected without passing through the frequency A in the regular order. When the setting in an inverse order is possible, however, it is not necessary to select the frequency A but the frequency C can be selected directly from the selection of the frequency E.

In the first modified example, by setting the selecting order of the using parameter values previously, only the switching operation enables the use of a parameter value according to the order. Accordingly, it can further speed up a diagnosis, in addition to the effect of the embodiment.

When the switching of the parameter values in an inverse order is possible, it is not necessary to take a round of the using parameter values, and therefore, it is possible to select a necessary parameter value more quickly.

As described in the embodiment, although the ultrasonic probe 11 and the input portion 14 may be integrated, the ultrasonic probe 11 may be provided with only a function of switching the parameter values, especially in the modified example. In this case, the probe 11 has to be provided with at least only one switch for switching the setting. Alternatively, in order to enable the switching in an inverse order, it has to be provided with two switches; one for the regular order and the other for the inverse order to this. Therefore, the ultrasonic probe 11 can be downsized. Further, since the ultrasonic probe 11 is generally used, always gripped by hand, while an operator makes a diagnosis, when a switch for switching the parameter values is provided in the ultrasonic probe 11, operational ability is further improved and a quicker diagnosis can be achieved.

SECOND MODIFIED EXAMPLE

This time, a second modified example in the embodiment according to the invention will be described with reference to the drawings. The second modified example is to make a group under a plurality of operational conditions, not to do under a single operational condition like in the above-mentioned embodiment. In this case, for example, when the operational conditions mean three parameters; transmitted pulse frequency, depth of viewing field, and photoimaging mode, if the values or the contents of the three parameters are determined, the scanning condition is uniquely determined. Hereafter, the description will be made, by way of example, in the case of making a group under the operational conditions including three parameters of transmitted pulse frequency, depth of viewing field, and photoimaging mode.

Figure 16:
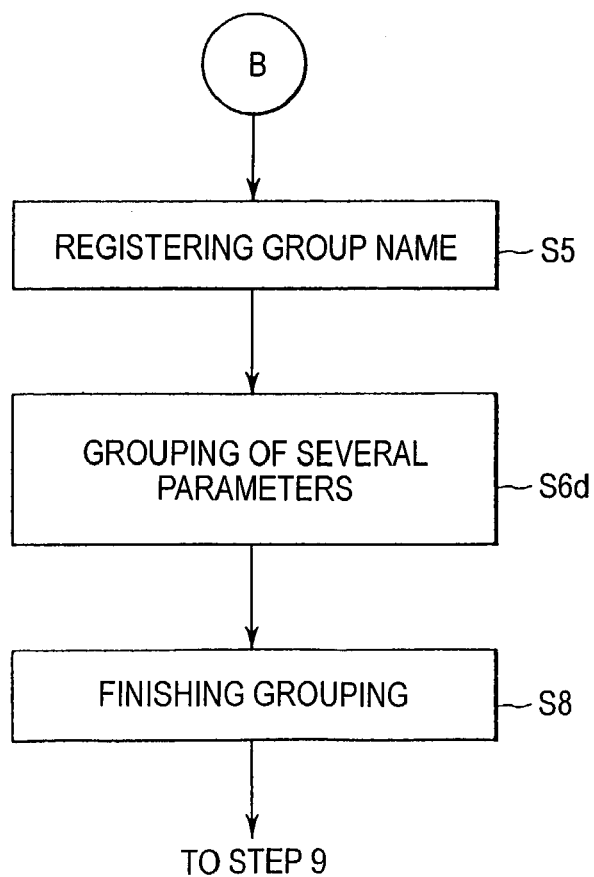
FIG. 16 is a flow chart showing the group selecting and registering processing in the second modified example.
Figure 17:
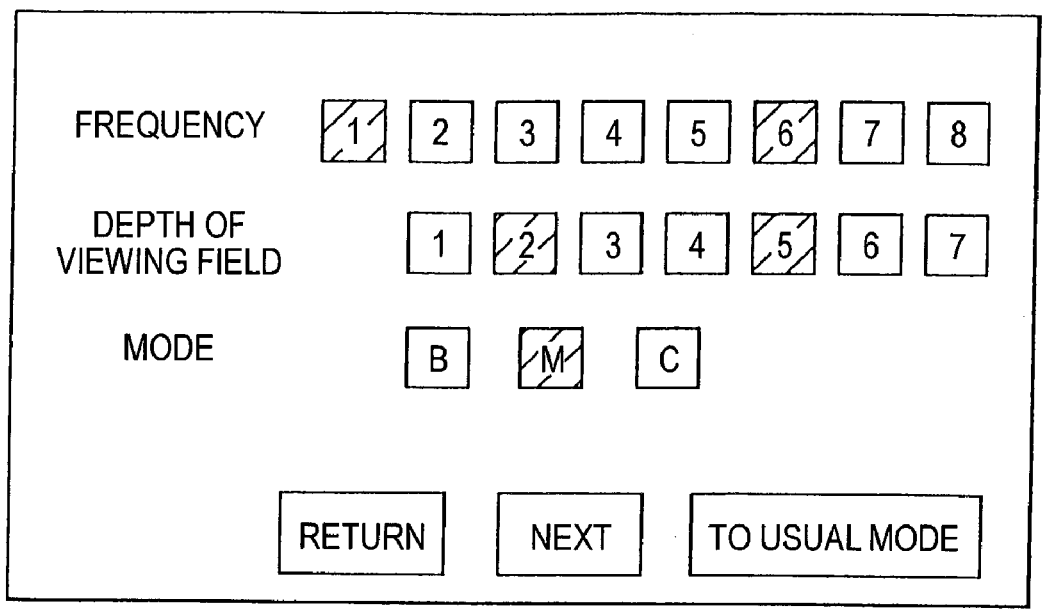
FIG. 17 is an example of the screen displayed in the grouping processing of a plurality of parameter values in the second modified example.

FIG. 16 is a flow chart showing the group selecting and registering processing in this modified example. In the figure, the processing up to Step S5 and the processing of Step S8 and later is the same as the processing shown in FIG. 3 and FIG. 4. FIG. 17 is an example of a screen displayed on the image display unit 13 in Step S6d of the flow chart shown in FIG. 16.

After registering the group name (Step S5) in FIG. 16, according to the contents of a screen displayed in FIG. 17, a plurality of parameter values are grouped (Step S6d). Namely, as illustrated in FIG. 17, the frequency includes 1 to 8 MHz in one MHz intervals, the depth of viewing field includes 1 to 8 cm in one cm intervals, and the mode includes B mode, M mode, and C mode (color mode). An operator selects a desired parameter value or desired contents while single-clicking only an item necessary for grouping with a mouse. In this modified example, as shown in the shaded portions, the operator selects the frequency of 1 and 6 MHz, the depth of viewing field of 2 and 5 cm, and the M mode.

In this modified example, all the combinations of the respective frequency, depth of viewing field, and mode selected as mentioned above are automatically grouped. Namely, when an operator selects as shown by the shaded portion in FIG. 17, it is grouped into the sum of four combinations including a combination of the frequency 1 MHz, the depth of viewing field 2 cm, and the M mode, a combination of the frequency 1 MHz, the depth of viewing field 5 cm, and the M mode, a combination of the frequency 2 MHz, the depth of viewing field 2 cm, and the M mode, and the like. This step 6d has a function of integrating Step 6a and Step 7 in the embodiment, which can make a group of each parameter value under the several kinds of parameters.

Needless to say, the range of the selectable parameter values is not restricted to the contents shown in FIG. 17.

The operational condition to be registered as the same group can be selected and cancelled in every mode, frequency, and depth of viewing field, any number of times until an operator pushes the button "Next", for example, shown in the right bottom of FIG. 17. As a canceling method, the object selected by the single click is again single-clicked, hence to be cancelled.

Continuously, the "Next" button is selected and the grouping is finished (Step S8).

Next, a desired group is selected (Step S9) in order to scan as shown in FIG. 4, and the parameter value to use is selected (Step S10). The selecting processing executed in this Step S10 is performed, for example, as follows, since this modified example is to make a group under a plurality operational conditions.

Figure 18:
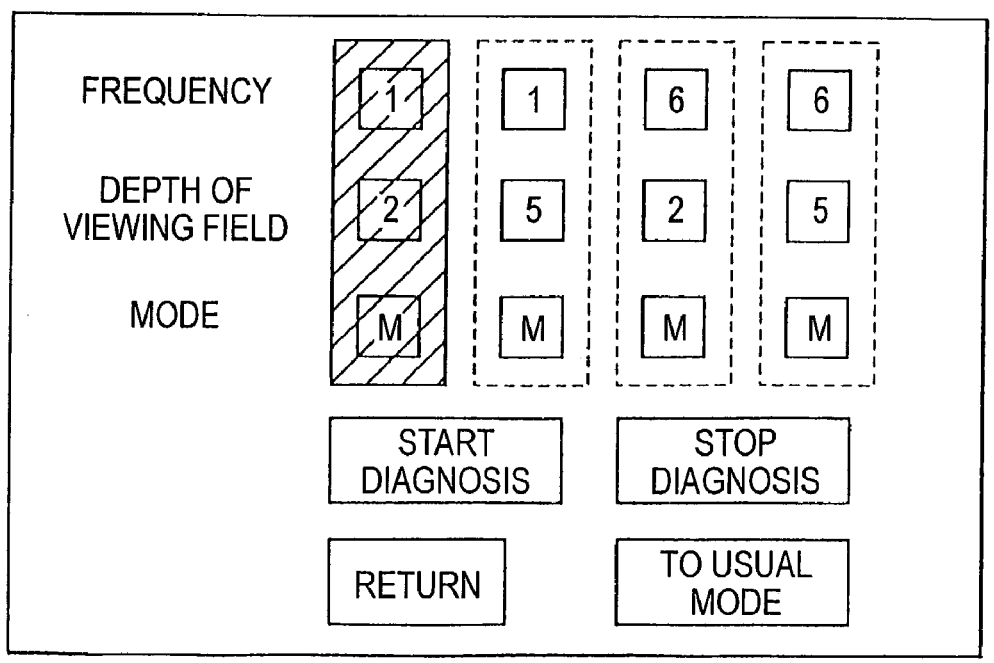
FIG. 18 shows an example of the screen displayed on the image display unit 13, in the selecting processing of parameter to use in the second modified example.

FIG. 18 shows an example of a screen displayed on the image display unit 13 in Step S10 in this modified example. In FIG. 18, each combination (surrounded by a dotted line) is aligned in the order of the combination of the frequency 1 MHz, the depth of viewing field 2 cm, and the M mode, the combination of the frequency 1 MHz, the depth of viewing field 5 cm, and the M mode, and the like from the left side on the screen. An operator can select a desired combination, hence to do scanning according to the combination. The shaded portion in FIG. 18 shows the corresponding combination selected by an operator.

It is also possible to change the selecting order, by the drag-and-drop operation as mentioned in the first modified example.

After the selection, the apparatus is set according to the combination, hence to start a diagnosis (Step S10).

In this modified example, the several parameters and parameter values including the frequency, the depth of viewing field, and the photoimaging mode can be grouped on one screen. Accordingly, in addition to the effect of the embodiment, the grouping operation can be performed more efficiently and more suitable setting of an apparatus depending on an operator or the condition of a patient can be performed quickly.

As mentioned above, although the invention has been described based on the embodiment and the modified examples, it is understood by those skilled in the art that various changes and modifications may be made within the spirit of the invention and that the above changes and modifications belong to the scope of the invention. For example, various changes are possible within departing from the spirit, as follows in the below (1) to (4).

(1) The invention includes a method for grouping the parameter values that are the conditions for setting an apparatus and a method for selecting a necessary parameter value from the grouped parameter values and using it. Accordingly, for example, such a modification is possible as repeating the steps depending on necessity or adding, deleting, or automating the steps. For example, a step for confirming whether the step is performed or not may be provided in each step. When using the two conditions at the same time, for example, when using the C mode and the B mode at the same time, the invention may be modified so that the necessary steps can be processed in parallel.

(2) Since the respective screens displayed on the image display unit 13 in the above-mentioned embodiment and modified examples are one example, the display screen is not restricted to the above.

(3) Although especially the ultrasonic apparatus is taken as an example in the above embodiment and modified examples, a setting method and setting means of a diagnostic apparatus including the process of grouping, selecting, and using a parameter value can be adopted to the other diagnostic apparatus.

(4) The hierarchical structure of grouping, namely, further grouping of the grouped parameter values is also possible. According to the hierarchical structure of grouping, even when a first group includes a lot of parameter values, the parameter values can be arranged gradually and a quick operation is possible. As mentioned in the second modified example, when making a group under a plurality of operational conditions, at first the frequency may be used to make a group, each group of the frequency is further grouped into every group of the depth of viewing field, and each group is further grouped in every photoimaging mode.

Further, the above embodiments can be performed in a proper possible combination, and in this case, the combined effects can be obtained. The above embodiments include various steps of inventions and various inventions can be extracted by a proper combination of the disclosed elements. For example, even if some elements are deleted from the whole elements described in the embodiments, when it is possible to solve the problem as mentioned in the section of the problems to be solved by the invention and at least one of the effects as mentioned in the section of the effects of the invention can be obtained, the structure with the above elements deleted therefrom can be extracted as the invention.

As mentioned above in detail, this invention can set a necessary apparatus quickly at a time of diagnosis. Accordingly, it is possible to improve the diagnostic efficiency of a patient and cope with an emergency diagnosis quickly.

What is claimed is:

1. A diagnosis apparatus comprising:
    a memory configured to store selectable values for a parameter which is usable in the diagnosis apparatus;
    a registration unit configured to register groups each of which includes at least one value of the parameter and at least one of which includes at least one value of the parameter selected by a user;
    a select unit configure to select a group from the registered groups and a value included in the selected group; and
    a driving unit configured to drive the diagnosis apparatus by using the selected value, wherein:
    the registration unit registers order of priority of the at least one value included in the at least one group; and
    the driving unit drives drive the diagnosis apparatus by using the selected value included in the selected group according to the priority order.

2. The diagnosis apparatus according to claim 1, wherein an attribute of the parameter is one of transmitted pulse frequency, imaging-mode, depth of viewing field, and physical index.

3. The diagnosis apparatus according to claim 1, wherein:
    the at least one of the groups includes at least one combination of values of at least two parameters which are usable in the diagnosis apparatus; and
    a driving unit configured to drive the diagnosis apparatus by using a selected combination included in the selected group.

4. The diagnosis apparatus, according to claim 1, which is one of an X-ray diagnosis apparatus, a computed tomography apparatus, a magnetic resonance imaging apparatus, and a nuclear medicine apparatus.

5. The diagnosis apparatus, according to claim 1, which is an ultrasound diagnostic apparatus.

6. The diagnosis apparatus, according to claim 5, further comprising:
    an ultrasonic probe which transmits an ultrasound wave based on a driving signal to an object to be examined and to receive an ultrasound wave reflected from the object to be examined; and
    the driving unit configured to drive the diagnosis apparatus by generating the driving signal to be supplied to the ultrasonic probe.

7. The diagnosis apparatus according to claim 1, further comprising a display unit which displays the at least one value of the parameter included in the selected group.

8. A controlling method of a diagnosis apparatus comprising:
    storing selectable values for a parameter which is usable in the diagnosis apparatus;
    first-selecting at least one parameter from the selectable values;
    registering at least one group which includes the at least one value selected in the first-selecting;
    second-selecting a group from the registered the at least one group and a value included in the selected group;
    driving the diagnosis apparatus by using the value selected in the second-selecting;
    registering order of priority of the at least one value included in the at least one group; and
    wherein the diagnosis apparatus is driven by using at least one value included in the selected group according to the priority order.

9. The controlling method of a diagnosis apparatus according to claim 8, wherein an attribute of the parameter is one of transmitted pulse frequency, imaging-mode, depth of viewing field, and physical index.

10. The controlling method of a diagnosis apparatus according to claim 9, wherein:
    the at least one group includes at least one combination of values of at least two parameters which are usable in the diagnosis apparatus; and
    the diagnosis apparatus is driven by using a selected combination included in the selected group.

11. The controlling method of a diagnosis apparatus according to claim 9, the diagnosis apparatus is one of an X-ray diagnosis apparatus, a computed tomography apparatus, a magnetic resonance imaging apparatus, and a nuclear medicine apparatus.

12. The controlling method of a diagnosis apparatus according to claim 9, the diagnosis apparatus is an ultrasound diagnostic apparatus.

13. The controlling method of a diagnosis apparatus according to claim 9, further comprising displaying the at least one value of the parameter included in the selected group.

14. The controlling method of a diagnosis apparatus according to claim 8, wherein the diagnosis apparatus is driven by generating the driving signal to be supplied to an ultrasonic probe.

* * * * *